United States Patent [19]

Hosmane et al.

[11] Patent Number: 5,599,959
[45] Date of Patent: Feb. 4, 1997

[54] ANALOGUES OF ACETYLSALICYLIC ACID AND NOVEL USES THEREOF

[75] Inventors: Ramachandra S. Hosmane, Columbia; Paddada R. Rao, Hampstead, both of Md.

[73] Assignee: University of Maryland, Baltimore, Md.

[21] Appl. No.: 382,300

[22] Filed: Jan. 31, 1995

[51] Int. Cl.$^6$ .................................................. C07C 233/00
[52] U.S. Cl. .......................... 554/63; 554/229; 560/76; 560/143; 560/163; 568/28; 568/31; 568/25; 568/425; 568/630; 564/123; 564/192; 562/405; 562/477; 562/478
[58] Field of Search .................................... 514/159, 165; 554/63, 229; 560/36, 52, 105, 76, 143, 163; 562/405, 477, 478; 568/25, 28, 31, 425, 630; 564/123, 192

[56] References Cited

U.S. PATENT DOCUMENTS

| | | | |
|---|---|---|---|
| 3,316,150 | 4/1967 | Faeges | 167/65 |
| 3,657,430 | 4/1972 | Shen et al. | 424/230 |
| 3,657,431 | 4/1972 | Shen et al. | 424/230 |
| 4,767,750 | 8/1988 | Jacquet et al. | 514/159 |

OTHER PUBLICATIONS

Covello et al, Chemical Abstracts, vol. 67, #13, 1967 63992.
Chemical Abstracts, vol. 53, #15, 14432a, 1959.
Reyes et al, Chemical Abstracts, vol. 101, #1, 1984.

Inoue et al, JP. J. Pharm., vol. 30, pp. 529–535, 1980.

*Primary Examiner*—Gary Geist
*Assistant Examiner*—Deborah D. Carr
*Attorney, Agent, or Firm*—Benjamin Aaron Adler

[57] ABSTRACT

The present invention provides a salicylate analogue having the structure

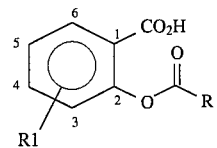

wherein R is selected from the group consisting of hydrogen, methyl, ethyl, n-propyl, i-propyl, n-butyl, i-butyl; pentyl, hexyl, heptyl, octyl, nonyl, decyl, undecyl, phenyl, naphthyl and cyclohexyl; wherein R1 is selected from the group consisting of hydrogen, a C1–C12 alkyl group, F, Cl, Br, I, $CO_2H$, $CONHR$, $CONR_2$, $CO_2R$, $C\equiv N$, CHO, COR, $SO_3$, $SO_2NHR$, $SO_2NR_2$, OH, OR, OCOR, SH, SR, OCONHR, $OCONR_2$, SCOR, SCONHR, $SCONR_2$ and NH2, NHR, NHCOR and NR2; and wherein R1 is in the 3-, 4-, 5- or 6-position, or a combination thereof. Also provided are various pharmaceutical compositions of the novel compounds of the present invention.

9 Claims, 4 Drawing Sheets n=0 ETHANOYL (ACETYL) SALICYLATE
n=1 PROPANOYL SALICYLATE
n=2 n-BUTANOYL SALICYLATE

ANALOGUES OF ACETYLSALICYLIC ACID AND NOVEL USES THEREOF

BACKGROUND OF THE INVENTION

1. Field of the Invention

The present invention relates generally to the fields of cardiovascular medicine and the chemistry of salicylates. More specifically, the present invention relates to novel analogues of acetylsalicylic acid and novel uses thereof.

2. Description of the Related Art

There is little literature other than the work of Reinhart and Chien (1986) concerning the effect of salicylates on rheological properties of red blood cells. Reinhart and Chien incubated red blood cells in vitro with very high concentrations (from 7.5 mM to 120 mM) of sodium salicylate, and found that there was a considerable decrease in the mean cell transit times of red blood cells while flowing through narrow capillaries. This observation is qualitatively in agreement with a more recent clinical study involving intake of aspirin by ten healthy human subjects (vide infra). However, the important difference between the two results is that the clinical study dealt with a salicylate concentration of the order of only 0.7 mM in whole blood, in addition to not accounting for adsorption of aspirin by tissues other than red blood cells. Furthermore, whereas no morphologic changes were observed in the red cells from their diskocyte form in the clinical study, Reinhart and Chien observed a definite echinocytic transformation. In fact, the latter researchers cite the change in morphology, i.e., the development of excess surface area, as the cause for the ease of flow of the red cells through the capillaries. This phenomenon of large shape changes at the high salicylate concentrations is but an extreme limit of the process that begins at the lower concentrations, namely the alteration of the membrane constitution and a lowering of the membrane viscoelastic properties. A speculative mechanism is that aspirin might acylate the membrane and this would not be unreasonable, based on the documented chemical property of aspirin to acylate proteins, including hemoglobins (Zaugg, et al., 1980).

Aspirin, a most common household drug, has long been known to improve blood circulation but the mechanism by which it does so has largely been a mystery. It is well known that the narrowing of arteries, resulting from the build-up of fatty acids, cholesterol, and scar tissues (atheroscerosis) inside the walls of the arteries, is one of the major factors responsible for inadequate blood supply or circulation (ischemia) that leads to major pathologies of the industrialized western world, such as heart attack (myocardial infarction), cerebrovascular disease (stroke or apoplexy), cramping pain of leg and calf muscles (intermittent claudication), recurrent chest pain (angina pectoris) and dry gangrene.

The prior art is deficient in the lack of effective means of decreasing the mean cell transit time of erythrocytes and thereby treating various cardiovascular diseases. The present invention fulfills this longstanding need and desire in the art.

SUMMARY OF THE INVENTION

In one embodiment of the present invention, there is provided a salicylate analogue having the structure

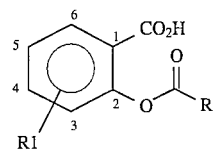

wherein R is selected from the group consisting of hydrogen, methyl, ethyl, n-propyl, i-propyl, n-butyl, i-butyl; pentyl, hexyl, heptyl, octyl, nonyl, decyl, undecyl, phenyl, naphthyl and cyclohexyl;

wherein R1 is selected from the group consisting of hydrogen, a C1–C12 alkyl group, F, Cl, Br, I, $CO_2H$, $CONHR$, $CONR_2$, $CO_2R$, $C\equiv N$, CHO, COR, $SO_3R$, $SO_2NHR$, $SO_2NR_2$, OH, OR, OCOR, SH, SR, OCONHR, $OCONR_2$, SCOR, SCONHR, $SCONR_2$ and $NH2$, NHR, NHCOR and $NR2$;

and wherein R1 is in the 3-, 4-, 5- or 6-position, or a combination thereof.

In another embodiment of the present invention, there is provided a pharmaceutical composition, comprising the novel salicylate compounds of the present invention and a pharmaceutically acceptable carrier.

In yet another embodiment of the present invention, there is provided a method of treating a vascular pathophysiological state in a human, comprising the step of administering a therapeutically effective dose of the compositon of claim 2 to said human.

In another embodiment of the present invention, there is provided a method of decreasing mean cell transit time of erythrocytes in a blood vessel in a human, comprising the step of administering a pharmacologically effective dose of the compositon of claim 2 to said human.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows a schematic of the capillary system used herein.

DETAILED DESCRIPTION OF THE INVENTION

Figure 1:
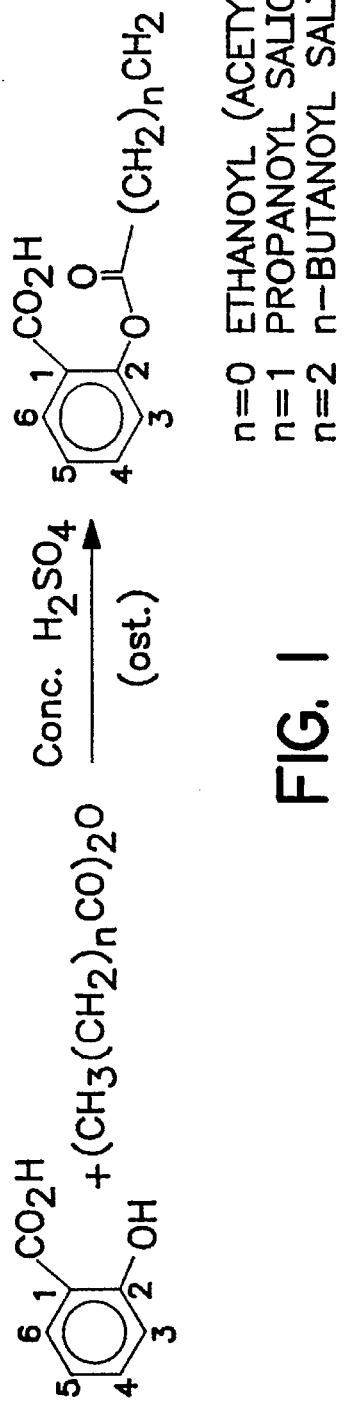
FIG. 1 shows the synthetic route for two of the acyl salicylates of the present invention: n=0 is ethanoyl (acetyl) salicylate; n=1 for propanoyl salicylate; and n=2 is n-butanoyl salicylate.

The present invention demonstrates that the intake of aspirin results in the decrease of membrane viscoelasticity of red blood cells, which enables them to flow through narrow capillaries with greater ease, thereby lowering their mean cell transit time. In addition, there is a direct correlation between increased lipophilicity of salicylates (aspirin analogues), decreased mean cell transit time, and decreased viscoelasticity of red cell membranes. The effect of salicylate on mean cell transit time is dependent upon the age of the red blood cell. To this end, the present invention shows isolated red blood cells incubated in vitro with a series of synthetic salicylates possessing varying degrees of lipophilicity, and showing the resulting changes in the mean cell volume (mean cell volume), as well as the capillary transit times (mean cell transit time) for these red blood cells. The present invention also shows a mechanical analysis of the above capillary flow data to relate mean cell transit time with the modulus of shear elasticity (G) and bending stiffness (B) of red cell membrane as a function of exposures to salicylate treatment. An analysis on the capillary flow data that was gathered in a clinical study involving aspirin intake by ten healthy individuals indicates that both G and B decrease with aspirin treatment. The present invention also compares the above indirect deduction of membrane mechanical properties with those obtained by the more direct but much more time-intensive, micropipette method. The latter method also enables assessment of red cell membrane shear viscosity. The present invention also shows a statistical analyses of the three sets of data: lipophilicity, mean cell transit time, and membrane viscoelastic properties. The present invention also determines if the hypothesized effect of salicylate on mean cell transit time is further dependent upon the age of red blood cells, i.e. if the changes are uniform or if they are more localized to fast or slow moving fractions of red blood cells, since age can be correlated to the rate of flow of red blood cells. For this, distributions of mean cell transit time values before and after salicylate treatment are compared for faster and slower fractions of red blood cells.

The present invention shows that the adsorption of lipophilic salicylate into the cell membrane leads to the lowering of both the membrane modulus of shear elasticity (G) and the membrane bending stiffness (B) in a manner analogous to monolayers wherein the surface pressure decreases with the doping of the membrane with foreign gaseous species (Goodman et al., 1991). While changes in the membrane shear viscosity and the cytoplasmic viscosity may also occur, they do not play a significant role in the mechanics of the capillary flow of red blood cells. Similarly, the mean cell volume is not a significant factor in the present invention. Reinhart and Chien indicated that close to a salicylate concentration of 0.1 mM, where the novel analogues of the present invention were effective, there is no change in the mean cell volume or surface area within graphical accuracy.

There is evidence that aspirin indeed gets adsorbed into the cell membrane. There is also evidence of a positive correlation between the amount of membrane adsorption and the lipophilicity of salicylate. For example, it was observed that the adsorption of n-propyl salicylate into oral-mucosal membrane of a hamster cheek pouch in vivo was considerably higher as compared with that of aspirin.

The effect of salicylate on mean cell transit time and concomitant changes in the red cell mechanical properties underscores the present invention. In contrast, the present invention cannot be attributed to such plausible factors as the activity of platelets or differences in mean cell volume, pH or other experimental conditions before and after aspirin treatment. For example, it can be shown that the higher mean cell transit time prior to aspirin treatment was not due to capillary occlusion by activated platelets. Any such occlusion would have resulted in an increase in mean cell transit time so large (from the additional pressure-drop versus capillary size relation determined by Hochmuth and Sutera, 1970) that it would have been discarded. Besides, the initially low relative concentration of platelets, and their subsequent removal through repeated washing of the suspension would have all but eliminated the possibility of the capillary occlusions from occurring in the first place.

Similarly, mean cell volume, pH, temperature and other flow parameters cannot explain the present invention, because the same experimental conditions including the buffer stock and polycarbonate capillaries (cleaned by ultrasonication) were employed before and after aspirin treatment. Further, the hematocrit dilution to 1% would have overcome any possible mean cell volume perturbation developed in the body. Indeed, the experimental data of Reinhart and Chien (1986) indicates a nearly constant mean cell volume at low salicylate concentration.

Thus, the present invention demonstrates that mean cell transit time decreases because of a decrease in the membrane viscoelasticity resulting from an adsorption of the salicylate into the lipid bilayer. A decrease in the membrane stiffness would lead to a decrease in the flow resistance experienced by red cells, and hence, a decrease in mean cell transit time. Furthermore, since the adsorption of salicylates into lipid bilayers would be somewhat dependent upon lipophilicity of salicylates, there is a three way correlation between mean cell transit time, viscoelasticity and lipophilicity.

The present invention demonstrates that the treatment of aspirin alters the elasticity (deformability) of red blood cells such that they flow through narrow arteries with greater ease. The present invention further shows that the analogues of aspirin which bind stronger to red blood cells than aspirin enable the cells to flow through these narrow blood vessels even faster.

Therefore, the present invention has implications in the development of therapy to treat these major diseases, all of which have origins in poor blood supply or circulation. The present invention involves synthesizing and probing those analogues of aspirin that have the optimal effect in reducing the elastic properies of red blood cells with consequent greatest ease of flow through clogged arteries.

Drug(s) are needed to prevent or treat heart attack, stroke, recurring chest pain, cramping pain of leg and calf muscles, and dry gangrene. The present invention discloses aspirin analogues which are useful as a therapy to prevent or treat heart disease, stroke, painful leg and calf muscles, chest pain, and dry gangrene.

Thus, the present invention discloses pharmaceutical compositions containing the salicylate analogue of the present invention and a pharmaceutically acceptable carrier. Representative examples of suitable salicylate analogues include benzoic acid, 2-(1-oxo-2-methylpropoxy), benzoic acid, 2-(1-oxopentyl)oxy, benzoic acid, 2-(1-oxo-3-methylbutyl)oxy, benzoic acid, 2-(1-oxoheptyl)oxy, benzoic acid, 2-(1-oxodecyl)oxy, benzoic acid, 2-(1-oxoundecyl)oxy, benzoic acid, 2-(cyclohexylcarbonyl)oxy, benzoic acid, 2-benzoyloxy, benzoic acid, 2-(1-naphthoyl)oxy, benzoic acid, 5-fluoro-2-(1-oxobutyl)oxy, benzoic acid, 2-(1-oxononyl)oxy, benzoic acid, 5-fluoro-2-(1-oxobutyl)oxy, benzoic acid, 5-chloro-2-(1-oxobutyl)oxy, and benzoic acid, 2,6-di(1-oxobutyl)oxy.

The present invention also is directed to a method of decreasing mean cell transit time of erythrocytes in a blood vessel in a human, comprising the step of administering a pharmacologically effective dose of the pharmaceutical compositon of the present invention to said human. Generally, the comoposition is administered in a dose of from about 1 mg/kg to about 20 mg/kg.

The present invention also is directed to a method of treating a vascular pathophysiological state in a human, comprising the step of administering a therapeutically effective dose of pharmaceutical compositon of the present invention to said human. Generally, the comoposition is administered in a dose of from about 1 mg/kg to about 20 mg/kg. Representative examples of vascular pathophysiological state include heart disease, stroke, painful leg and calf muscles, chest pain, atherosclerosis and dry gangrene.

It is specifically contemplated that pharmaceutical compositions may be prepared using the novel compounds of the present invention. In such a case, the pharmaceutical composition comprises the novel compounds of the present invention and a pharmaceutically acceptable carrier. A person having ordinary skill in this art would readily be able to determine, without undue experimentation, the appropriate dosages and routes of administration of the novel compounds of the present invention.

The following examples are given for the purpose of illustrating various embodiments of the invention and are not meant to limit the present invention in any fashion.

EXAMPLE 1

Figure 2A:
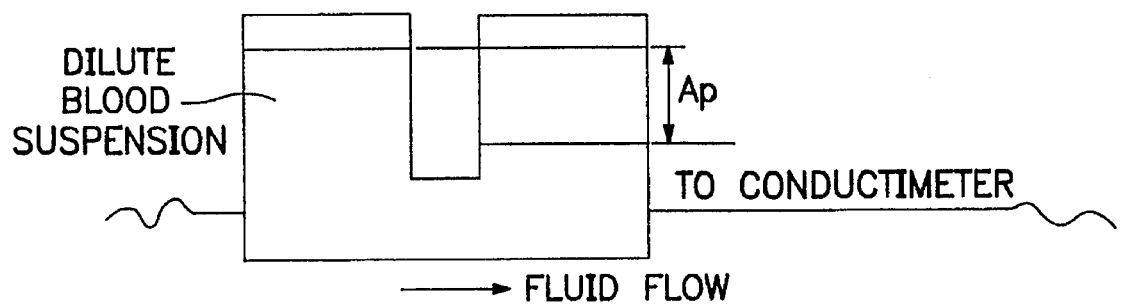
In FIG. 2(a), the dilute blood sample flows through each of the capillaries due to the applied hydrostatic pressure head, $\Delta p$. The hematocrit was kept sufficiently low (less than 0.1%) so that the red blood cells flow through the capillary system one at a time. The electrodes on either side of the capillaries detect a drop in conductance due to the presence of a cell.
Figure 2B:
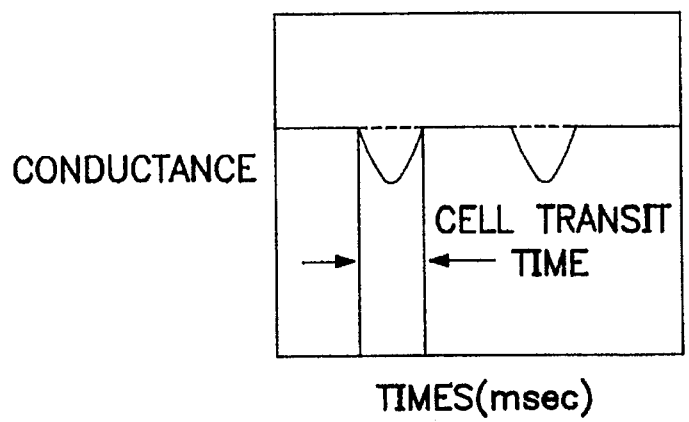
In FIG. 2(b), the period of drop in the electrical conductance is considered the cell transit time. Approximately, one thousand cells are examined per donor to obtain the MCTT.

Blood samples were drawn from ten healthy human adult volunteers in 10 mL vacutainers containing EDTA as an anti-coagulant. Red cells from each one of these samples were washed thrice and resuspended in PBS at less than 1% hematocrit. The resulting suspension was introduced into a polycarbonate capillary system and the mean transit time was determined for approximately 2000 cells. FIG. 2 shows a schematic of the capillary system used herein. The capillaries were 5 μm in diameter and 15 μm in length, and were cleaned by ultrasonication prior to each flow run. Data was gathered at a pressure difference of 2 cm of water across the 15 μm long capillaries. This pressure gradient was such that the study could be carried out fairly rapidly to avoid the settling of red cells in the upstream reservoir. For the capillary flow studies, blood samples from the normal human adults were drawn intravenously into 5 ml vacutainers containing anticoaggulant (EDTA) and were subsequently washed thrice with a phosphate buffered saline solution. A final blood sample of 5 ml of approximately 0.1% hematocrit was prepared using PBS and a freshly prepared salicylate solution so that the resulting solution had an osmolality of 290 mOsmol/kg and a pH of 7.4. The salicylate concentration was 0.05 mM in half the samples and 0.005 mM in the other half. This blood sample was subsequently introduced into a flow system consisting of thirty parallel polycarbonate capillaries each of dimensions described above. The flow through the capillaries was initiated by elevating the upstream reservoir level by 2 cm relative to the downstream level. The associated pressure differential remained constant throughout the experiment (which lasted for about a minute) due to the extremely low bulk flow rate through the capillary system. The transit time (and their average, MCTT) of approximately one thousand erythrocytes taken from the control and each of the salicylate suspensions were measured at a fixed pressure gradient after thirty minutes of incubation at room temperature. Mean Cell volume was measured using a Coulter Multisizer II with a 1000 channelyzer interfaced to an IBM PS/2 model computer calibrated with Coulter Diagnostics blood standards. Washed, packed cells were diluted by a factor of 200,000 in PBS to give a cell volume of normal discoid cells.

Figure 3:
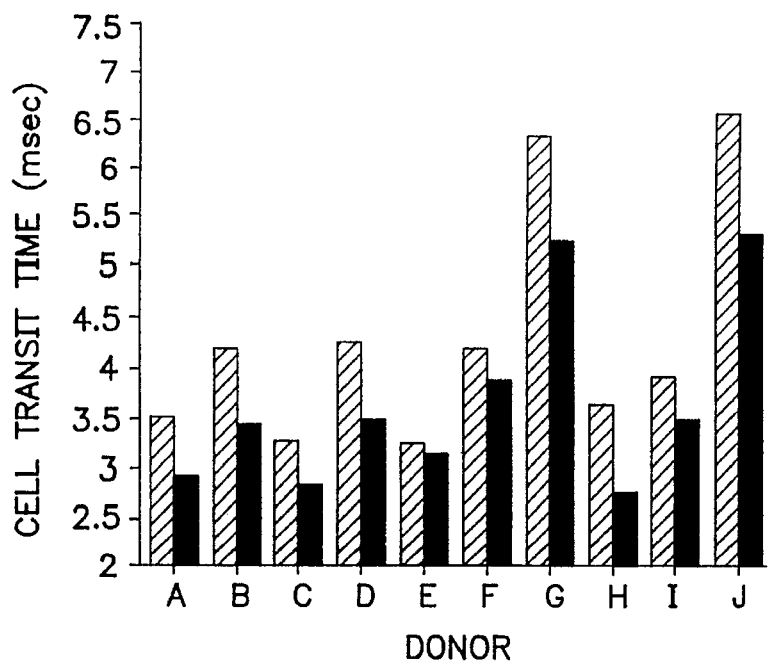
FIG. 3 shows the effect of 650 mg of aspirin on the mean transit time of normal human red blood cells.

Each subject ingested 650 mg of aspirin immediately after the blood drawing, and 3 hours later donated a second sample of blood. The measurement of cell transit times was repeated following the same procedure as before. Statistically, a highly significant decreases in mean cell transit time ($p<0.01$) was observed after the aspirin treatment (see FIG. 3). FIG. 3 shows that intake of 650 mg of aspirin by healthy human subjects leads to a highly significant (to 1% level) decrease in the mean transit time of red blood cells in 5 μm diameter polycarbonate capillaries. These differences were significant despite a considerable donor to donor variation.

EXAMPLE 2

Two analogues of aspirin were then synthesized which were slightly more lipophilic than aspirin. FIG. 1 shows the synthetic route for two of the acyl salicylates of the present invention. For salicylate preparation, one equivalent of salicylic acid was dissolved in 2–3 equivalents of the appropriate acid anhydride in the presence of catalytic amounts of concentrated sulfuric acids (approximately 10 drops). The mixture was stirred at room temperature for 0.5 hours and then at 50°–70° C. for 2 hours. The reaction mixture was poured into ice water and the precipitated product was filtered in vacuo, dried and recrystallized from the appropriate solvent.

The physico-chemical data for the products of FIG. 1 was as follows: ethanoyl (acetyl) salicylate was recrystallized from toluene; mp 136°–138° C. as described by Zaugg et al., *J. Biol. Chem.*, 255:2816–2821, 1980; $^1$H NMR (CDCl$_3$) δ2.35 (s, 3H), 7.15 (d, J=8.1 Hz, 1H), 7.36 (app. t, J=7.8 & 8.1 Hz, 1H), 8.14 (d, J=7.3 Hz, 1H). Propanoyl salicylate was recrystallized from toluene; mp 94°–96° C. as described by Zaugg et al., $^1$H NMR (CDCl$_3$) δ1.21 (t, J=7.5 Hz, 3H), 2.66 (q, J=7.5 Hz, 2H), 7.14 (d, J=7.8 Hz, 1H), 7.37 (t, J=7.8 Hz, 1H), 7.64 (t, J=7.3 Hz, 1H), 8.13 (d, J=7.5 Hz, 1H). n-Butanoyl salicylate was recrystallized from toluene; mp 76°–78° C. as described by Zaugg et al., $^1$H NMR (CDCl$_3$) δ1.05 (t, J=7.5 Hz, 3H), 1.82 (m, 2H), 2.61 (t, J=7.5 Hz, 2H), 7.14 (d, J=8.1 Hz, 1H), 7.34 (t, J=7.5 Hz, 1H), 7.61 (t, J=7.5 Hz, 1H), 8.13 (d, J=7.8 Hz, 1H).

Figure 4:
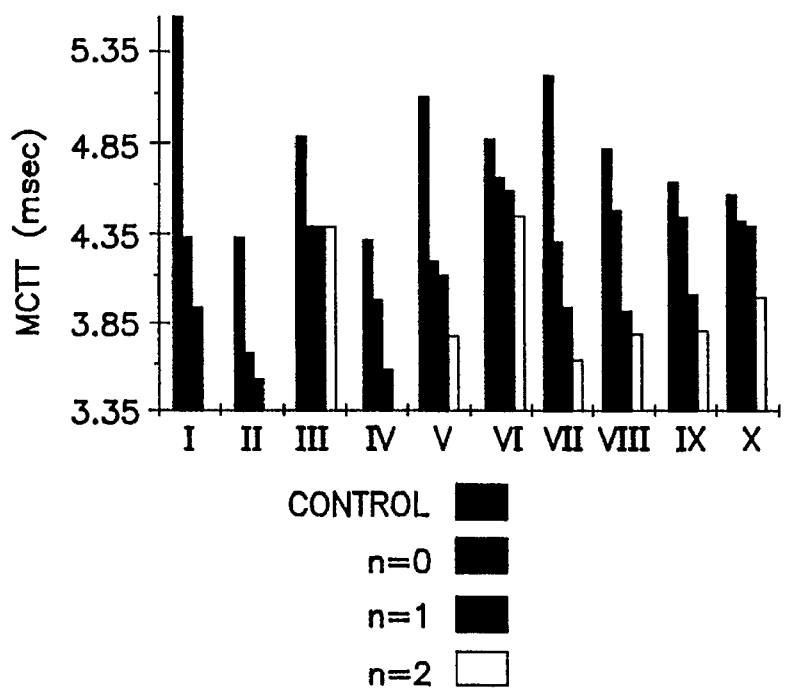
FIG. 4 shows the correlation between mean cell transit time and lipophilicity. Mean cell transit time decreases with each additional —$CH_2$ group.
Figure 5:
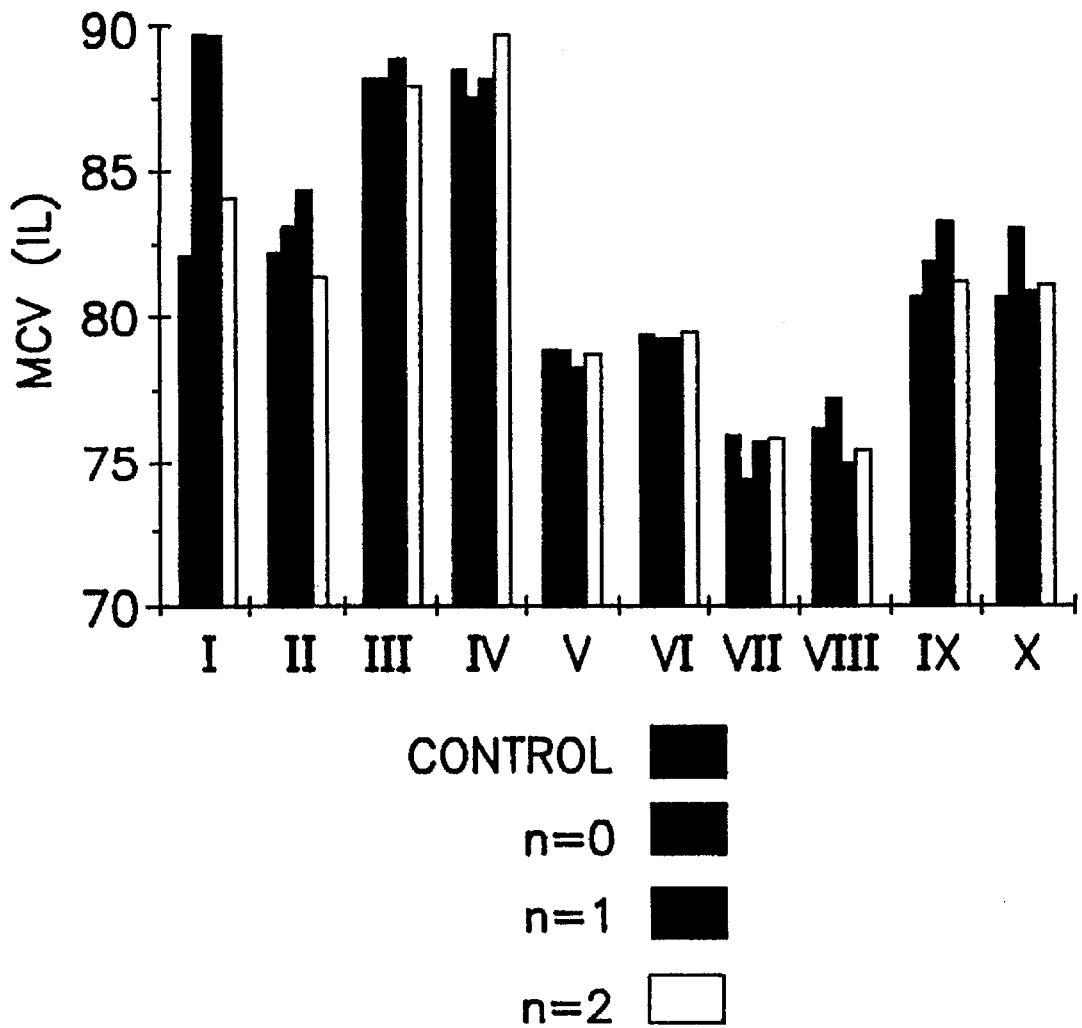
FIG. 5 shows that the mean cell volume does not decrease with salicylate treatment.

These analogues were incubated in vitro with red blood cells collected from healthy human adults of diverse races representing European, African, and Asian descents. Following the protocol described below, the mean cell transit time data was obtained for each of ten red blood cell samples, using aspirin and its two analogues, along with control (no aspirin or its analogue). As can be seen from FIG. 4, there is a statistically significant decrease (p<0.01) in the mean cell transit time with aspirin (n=0) as compared with the control (no aspirin or its analogue). Further decrease of mean cell transit time of each of the aspirin analogue (n=1 & 2) from control is even more significant statistically as evidenced by the computed p value which is <0.005. This is especially important since an increase of only one or two $CH_2$ groups would not significantly alter the lipophilic character of aspirin.

Table 1 shows the MCTT data in milliseconds for red cells placed in control solution containing ethanoyl (acetyl) salicylate (n=0), propanoyl salicylate (n=1), and n-butanoyl salicylate (n=2).

TABLE 1

Mean Cell Transit Time, MCTT (msec)

| Sample | Control | n = 0 | n = 1 | n = 2 |
|---|---|---|---|---|
| 1 | 5.50 | 4.31 | 3.91 | Lysis |
| . | 4.29 | 3.66 | 3.51 | Lysis |
| . | 4.86 | 4.38 | 4.57 | 4.35 |
| . | 4.29 | 3.96 | 3.56 | 3.57 |
| . | 5.08 | 4.17 | 4.09 | 3.76 |
| . | 4.83 | 4.63 | 4.56 | 4.42 |
| . | 5.17 | 4.29 | 3.92 | 4.61 |
| . | 3.79 | 4.45 | 3.89 | 3.76 |
| . | 4.61 | N/D | 3.97 | 4.18 |
| 10 | 4.52 | 4.39 | 4.46 | 3.95 |
| mean+ (of 3–10) | 4.64± 0.42 | 4.32± 0.20 | 4.13 ± 0.34 | 4.08 ± 0.35 |
| p level | | 0.01 | 0.005 | 0.005 |

EXAMPLE 3

To confirm that the above changes in mean cell transit time were not due to changes in mean cell volume, mean cell volume measurements were also performed. There was no concomitant decrease in mean cell volume with decreasing mean cell transit time. Instead, mean cell volume appears to increase slightly in most cases. Thus, the salicylate alters the red cell deformability through alteration of the membrane elastic properties and not through changes in the mean cell volume.

The relationship between salicylate concentration and the red cell characteristics was also demonstrated. The concentration of 0.5 mM (the lower end of the salicylate concentration in Reinhart and Chien's work) was, apparently, too strong. Practically all red cells lysed at this concentration of n-propylsalicylate. Mean cell transit time data were obtained for all salicylates only at or below a concentration of 0.05 mM. However, between 0.05 mM and 0.005 mM there was no significant difference in mean cell transit time or in mean cell volume. That there was no dependence of concentration of salicylate on the flow characteristics of red blood cells is of considerable significance. Since there are limited (amino) sites to which a particular salicylate can bind within the membrane proteins, these sites become saturated as the salicylate concentration increases. Thus, the ensuing perturbation of the mechanical elastic property (shear modulus of elasticity) may not be expected beyond a certain concentration of salicylate, whereas changes in the membrane fluidity (shear modulus of viscosity) which may result from the adsorption of salicylate into the lipid bilayer may not reach an asymptote as quickly. Therefore, the changes in mean cell transit time due to salicylate treatment were mainly due to the salicylate (acyl)-protein (amino) interaction which causes a disruption of the membrane protein cytoskeleton, the disruption being greater in the case of more lipophilic salicylates. This consequently leads to a decrease in the shear modulus of elasticity, possibly, along with other more complex effects, including perturbation of ionic groups on the membrane proteins, enzymic interactions, etc.

On the other hand, at higher salicylate concentrations, one can expect a greater damage in the lipid bilayer as well, which will lead to a decrease in the membrane shear viscosity and an increase in the membrane surface area. Both of these changes will lead to greater cell deformability and lower mean cell transit time. Indeed, the improved red blood cells flow rate as observed by Reinhart and Chien at salicylate concentrations between 7.5 and 120 mM, which is several orders of magnitude higher than the concentration employed in the present invention, can be explained by this mechanism. Reinhart and Chien observed the surface area to increase with increasing salicylate concentration, and if their data were to be extrapolated down to the concentrations employed in the present invention, one would find almost no change in the surface area.

Morphological statistics was also gathered from the video recording of the above samples. The percentage of echinocyte form of red blood cells among diskocytes for each salicylate treatment was recorded. No particular trend in morphologic characteristics of the cells was observed.

Besides the assessment of mean cell transit time, mean cell volume and morphological characteristics, it was also possible to make measurements of hemoglobin concentrations of the red blood cells and thereby determine changes in the cytoplasmic viscosity after salicylate incubation. However, that is not necessary, since the cell transit time that the capillary flow system provides is actually the time taken by the cell after it has completely entered the capillary and has undergone its entire deformation. This means that if one assumes an axisymmetric steady flow, then both the membrane and cytoplasmic viscosities drop out from the analysis and there is evidence that axisymmetric flow assumption is quite appropriate.

EXAMPLE 4

Synthesis of Salicylates

A series of salicylates (analogues of aspirin) were synthesized which possess differing degrees of lipophilicity as measured by their partition coefficients between water and octanol. Chemical modifications of aspirin are made by changing R and R1 groups as shown. For example, for a particular set of lipophilic R groups, e.g. $(CH_2)_6CH_3$, introduction of additional lipophilic and/or hydrophilic R1 groups at other positions of the benzene ring enhances or lowers the mean cell transit time and membrane elasticity. The following salicylates were synthesized and their rheological properties shown. The first list of compounds contains compounds with lipophilic modifications introduced only in the R group, while keeping R1 as H.

After synthesizing and showing the rheological properties of compounds from the first list above, the most promising lipophilic R group are used. These compounds are used to show as to what position of the benzene ring, proximal or distal to the carboxy and/or acyloxy functional group, would be most appropriate for further lipophilic and/or hydrophilic substitution, if at all.

Lipophilic Salicylates Synthesized

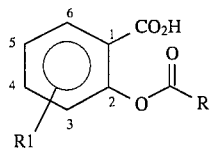

wherein R is selected from the group consisting hydrogen, methyl, ethyl, n-propyl, i-propyl, n-butyl, i-butyl; hexyl, heptyl, octyl, nonyl, decyl, undecyl, phenyl, naphthyl and cyclohexyl;

wherein R1 is selected from the group consisting of hydrogen, a C1–C12 alkyl group, F, Cl, Br, I, $CO_2H$, $CONHR$, $CONR_2$, $CO_2R$, $C\equiv N$, CHO, COR, $SO_3R$, $SO_2NHR$, $SO_2NR_2$, OH, OR, OCOR, SH, SR, OCONHR, $OCONR_2$, SCOR, SCONHR, $SCONR_2$ and NH2, NHR, NHCOR and NR2;

and wherein R1 is in the 3-, 4-, 5- or 6-position, or a combination thereof.

The compounds of the present invention were synthesized using a general procedure that is modeled after the synthesis of aspirin. Thus, salicylic acid is condensed with the appropriate acid anhydride in the presence of an acid catalyst to obtain the corresponding acylsalicylic acid. While a variety of acid catalysts have been reported, e.g., sulfuric, phosphoric, and perchloric acid; polyphosphoric acid (PPA) seems to give the best results, with yields of aspirin ranging >97%. Most of the necessary acid anhydrides are commercially available. Thus, propionic anhydride for the synthesis of I (R=Et), butyric anhydride for II (R=n-Pr), isobutyric anhydride for III (R=i-Pr), valeric anhydride for IV (R=n-Bu), caproic anhydride for VI (R=Pentyl), heptanoic anhydride for VII (R=Hexyl), decanoic anhydride for X (R=Nonyl), dodecanoic anhydride for XII (R=Undecyl), and benzoic anhydride for XIII (R=Phenyl) are commercially available (Aldrich). If the acid anhydrides were not commercially available, they were prepared from the corresponding acid chlorides by reactions with alkali metal salts of the same acids. Thus, isovaleric anhydride for the synthesis of V (R=i-Bu), octanoic anhydride for VIII (R=Heptyl), nonanoic anhydride for IX (R=Octyl), undecanoic anhydride for XI (R=Decyl), 1- and 2-naphthoic anhydride for XIV (R=Naphthyl), and cyclohexanoic anhydride for XV (R=Cyclohexyl) were prepared, respectively, from isovaleryl chloride, octanoyl chloride, nonanoyl chloride, undecanoyl chloride, 1- and 2-naphthoyl chloride and cyclohexane carbonyl chloride, all of which are commercially available (Aldrich). Alternatively, salicylic acids were treated directly with the appropriate acid halides to obtain the desired products by adjusting stoichiometric ratio of the reactants and by carefully controlling the reaction conditions.

Compounds I, II, and III were synthesized from the respective 3-methyl-, 4-methyl-, and 5-methylsalicylic acids, available from Aldrich, by analogous acylation procedures described above for compounds of Table I. 6-Methylsalicylic acid, necessary for the synthesis of IV, was prepared by oxidation of 2,3-dimethylphenol (Aldrich) with potassium hydroxide. Such an oxidation procedure has been successfully employed for the synthesis of several o-hydroxybenzoic acids from the corresponding polymethylphenols. Under the experimental conditions employed, the methyl group ortho to the hydroxyl is specifically oxidized, while leaving intact all other methyl groups on the benzene ring. Alternatively, 6-methylsalicylic acid is prepared by the reaction of the sodium salt of m-cresol with carbon dioxide at 200°–250° C., followed by separation from a mixture containing its regio-isomer, 4-methylsalicylic acid, by chromatography or by fractional recrystallization. In this synthesis, a carboxy group is introduced ortho to the hydroxyl group. Such a procedure has been successfully employed to prepare 3,4,6-trimethylsalicylic acid from sodium 2,3,5-trimethylphenolate and 3,5,6-trimethylsalicylic acid from sodium 2,4,5-trimethylphenolate. Compounds V [CAS RN: 14484-24-3], VI [CAS RN: 14387-03-2], VII [CAS RN: 17514-03-3], and VIII [CAS RN: 3929-88-2] were synthesized using the literature procedures. Compounds IX and X is prepared by acylation of 3,5,6-trimethylsalicylic acid [CAS RN: 99186-48-8]and 3,4,6-trimethylsalicylic acid [CAS RN: 73074-12-1], respectively. Compound XI was prepared by acylation of 3,4,5-trimethylsalicylic acid which, in turn, can be prepared from 2,3,4-trimethylphenol [CAS RN: 526-85-2] by high temperature reaction with carbon dioxide as described above. Compound XII is prepared by acylation of 4,5,6-trimethylsalicylic acid which, in turn, was prepared by potassium hydroxide oxidation of sodium 2,3, 4,5-tetramethylphenolate [CAS RN: 78210-36-3]. The latter was also employed to prepare 3,4,5,6-tetramethylsalicylic acid by reaction with carbon dioxide at elevated temperature as described before. 3,4,5,6-Tetramethylsalicylic acid was also prepared by potassium hydroxide oxidation of pentamethylphenol [CAS RN: 2819-86-5] as described above. Acylation of 3,4,5,6-tetramethylsalicylic acid gives XIII.

Benzoic acid, 2-(1-oxobutyl)oxy was synthesized in a 25 ml three necked flask into which was placed 1.73 g (0.0125 mol) of salicylic acid and 4.95 g (5.1 ml, 0.0313 mol) of butyric anhydride at room temperature and the mixture was stirred for 10 minutes. After that, 4–5 drops of concentrated sulfuric acid was added and stirred at 45°–50° C. for 30 minutes. 4 ml of water was added at 50° C. in one portion and stirred for 10 minutes. The excess acid anhydride decomposes. 20 ml of ice water were added and the flask stood at room temperature overnight. The half-solid was separated and collected, recrystallized from toluene to obtain 1.35 g (64.9%) of white solid. mp 76°–78° C. $^1$H NMR (CDCl$_3$): δ1.05 (t, 3H), 1.82 (m, 2H), 2.61 (t, 2H), 7.14 (d, 1H), 7.34 (t, 1H), 7.61 (t, 1H), 8.13 (d, 1H).

Benzoic acid, 2-(1-oxooctyl)oxy was synthesized in a 25 ml three necked flask into which was placed 1.49 g (0.01 mol) of salicylic acid and 2.0 g of pyridine. 1.89 g (0.011 mol) of octanonyl chloride was added dropwise at 0° C. and the mixture was stirred for 5.5 hours at room temperature. After that, a solution of 9 ml water and concentrated HCl was added and stirred for 10 minutes. The solid was collected, washed with water successively, NaHCO$_3$ solution and water, dried and recrystallized from toluene to obtain 1.96 g (74.1%) of white solid. mp 77°–79° C. $^1$H NMR (CDCl$_3$): δ0.89 (t, 3H), 1.32 (m, 2H), 1.80 (m, 2H), 2.62 (t, 2H), 7.13 (d,1H), 7.34 (t, 1H), 7.62 (t, 1H), 8.12 (d, 1H).

Benzoic acid, 2-(1-oxododecyl)oxy was synthesized in a 25 ml three necked flask into which was placed 0.8 g (5.8 mmol) of salicylic acid and 1.36 g (3.6 mmol) of lauric anhydride and 1 ml of pyridine. The mixture was stirred for 18 hours at 50° C. After cooling, a solution of 15 ml water and 4 ml concentrated HCl was added and the mixture was extracted with ether. The ether layer was washed successively with water, NaHCO$_3$ solution and water and dried. The solvent was evaporated and the residue was recrystallized from hexanes to obtain 1.0 g (87%) of white solid. mp 47°–49° C. $^1$H NMR (CDCl$_3$): δ0.90 (t, 3H), 1.27–1.78 (m, 16H), 2.36 (m, 2H), 2.61 (t, 2H), 7.12 (d,1H), 7.33 (t, 1H), 7.60 (t, 1H), 8.11 (d, 1H).

Benzoic acid, 5-chloro-2-(1-oxobutyl)oxy was synthesized in a 25 ml three necked flask into which was placed 1.73 g (0.01 mol) of 5-chloro-salicylic acid and 4.75 g (4.9 ml, 0.03 mol) of butyric anhydride at room temperature and stirred for 10 minutes. Several drops of sulfuric acid was added dropwise and the mixture was stirred for 3 hours at 70°–75° C. Next, 4 ml of water was added at 70° C. and stirred for 15 minutes. 15 g of ice water was added and stirred for several minutes. The solid was collected, was washed with water, and recrystallized from hexanes to obtain 1.83 g (75.4%) of white solid. mp 121°–123° C. $^1$H NMR (CDCl$_3$): δ1.08 (t, 3H), 1.81 (m, 2H), 2.59 (t, 2H), 7.09 (d, 2H), 7.58 (d,1H), 8.08 (s, 1H), 9.74 (br. s, 1H).

The NMR spectral data for benzoic acid, 2-(1-oxobutyl)oxy, mp 76°–78° C., was $^1$H NMR (CDCl$_3$): δ1.05 (t, 3H), 1.82 (m, 2H), 2.61 (t, 2H), 7.14 (d, 1H), 7.34 (t,1H), 7.61 (t, 1H), 8.13 (d, 1H).

The NMR spectral data for benzoic acid, 2-(1-oxo-2-methylpropoxy), mp 94°–96° C., was $^1$H NMR (CDCl$_3$): δ1.36 (d, 6H), 2.86 (m, 1H), 7.12 (d, 1H), 7.32 (t,1H), 7.61 (t, 1H), 8.11 (d, 1H).

The NMR spectral data for benzoic acid, 2-(1-oxopentyl)oxy), mp 68°–70° C., was $^1$H NMR (CDCl$_3$): δ1.00 (t, 3H), 1.47 (m, 2H), 1.75 (m, 2H), 2.64 (t, 2H), 7.13 (d, 1H), 7.33 (t, 1H), 7.6 (t, 1H), 8.12 (d, 1H).

The NMR spectral data for benzoic acid, 2-(1-oxoheptyl)oxy), mp 61°–63° C., was $^1$H NMR (CDCl$_3$): δ0.82 (t, 3H), 1.34 (m, 6H), 1.68 (m, 2H), 2.60 (t, 2H), 7.11 (d, 1H), 7.33 (t, 1H), 7.59 (t, 1H), 8.10 (d, 1H).

The NMR spectral data for benzoic acid, 2-(cyclohexylcarbonyl)oxy, mp 123°–124° C., was $^1$H NMR (CDCl$_3$): δ1.27–1.39 (m, 2H), 1.52–1.72 (m, 4H), 1.86 (m, 2H), 2.13 (m, 2H), 2.62 (m, 1H), 7.11 (d, 1H), 7.36 (t, 1H), 7.61 (t, 1H), 8.09 (d, 1H).

The NMR spectral data for benzoic acid, 2-(benzoyl)oxy, mp 113°–115° C., was $^1$H NMR (CDCl$_3$): δ6.23–6.79 (m, 6H), 7.16–7.39 (m 3H).

The NMR spectral data for benzoic acid, 5-(fluoro-2-(1-oxobutyl)oxy, mp 94°–96° C., was $^1$H NMR (CDCl$_3$): δ1.08 (t, 3H), 1.81 (m, 2H), 2.62 (t, 2H), 7.12 (d, 1H), 7.32 (t, 1H), 7.81 (s, 1H), 9.8 (br.s., 1H).

Benzoic acid, 2,6-di(1-oxobutyl)oxy was synthesized as follows: in a 25 ml three necked flask was placed 1.54 g of 2,6-dihydroxy benzoic acid and 6.33 g (6.54 ml, 0.04 mol.) of propionic anhydride at room temperature and the mixture was stirred for 10 minutes. Afterwards, 9 drops of concentrated sulfuric acid (>98%) was added dropwise, and stirred at 45°–50° C. for 24 hours. Water (4 ml) at 50° C. in one portion and stirred for 15 minutes, and the excess anhydride was decomposed. Then 20 ml of water was added and extracted with ether (3×10 ml), washed with 2% NaHCO$_3$ solution and dried over anhydrous MgSO$_4$. After removing the solvent, the residue was separated by silica gel to give 0.75 g (22.5%) of the compound as a white solid, m.p. 73°–74° C. $^1$H NMR (CDCl$_3$): δ1.04 (t, 6H), 1.77 (m, 4H), 2.54 (t, 4H), 7.07 (d, 2H), 7.53 (t, 1H).

EXAMPLE 5

Incubation of Red Blood Cells with Salicylates

Blood samples are drawn from healthy human adult volunteers in 10 mL vacutainers containing EDTA as anticoagulant. After centrifugation at 1000×g for ten minutes, the plasma buffy coat and the uppermost red blood cells layer is removed. The red blood cells are washed three times and resuspended in phosphate buffered saline (PBS) solution.

Fresh stock solutions of acyl salicylate are prepared for every experiment, and the pH is adjusted to 7.4 with PBS. The red blood cells suspension is divided into several aliquots. The aliquots are centrifuged at 1000×g for 2–3 minutes to sediment red blood cells and generate the PBS supernatant. A calculated amount of the PBS solution is replaced by an appropriate volume of stock solution to obtain the desired acyl salicylate concentration and a hematocrit of 1%. These red blood cells suspensions are then incubated for 20 minutes at 37° C. and used immediately thereafter for all capillary flow and micropipette experiments.

EXAMPLE 6

The mean cell transit time data are verified both by the capillary flow system and the micropippette method. The micropipette apparatus requires a careful calibration of the diameter of individual pipettes which cannot be identically duplicated. This may lead to non-uniformity in the conditions among the samples. More important, the process of manually observing a large number of red cells and recording their transit time is both cumbersome and error prone. On the other hand, the capillary flow system approach yields the mean cell transit time data with greater accuracy, consistency and ease. Nevertheless, the micropipette supports the results based on the capillary flow system and the consequent data analysis.

Two different types of analyses of data are collected from the capillary flow experiments. First, an analysis of the mechanics of the red cell membrane as it flows through a rigid capillary is shown. The outcome of this analysis are two elastic properties (averaged over the cell population), namely, membrane shear modulus, G and the membrane bending rigidity, B. These two elastic properties are calculated before and after salicylate treatment. Second, a statistical analysis of the distribution of the cell transit times to determine if the changes in mean cell transit time due to salicylate are predominant in any one group of the population or if salicylate affects the cell population uniformly.

EXAMPLE 7

Capillary Flow Mechanics Analysis

The red cell is modeled as a cylindrical axisymmetric membrane separated from the capillary wall by a narrow lubrication layer of PBS (phosphate-buffered saline) solution. While a typical red cell in a capillary flow does not display axisymmetry, there is sufficient evidence (for example, Hsu and Secomb, 1989) that axisymmetric models predict well the dynamics of experimentally measured flows. The upstream and downstream end-surfaces of the cell are assumed to be sections of spheres. The exact shape of the end-caps is not important since it has been shown that the pressure drop across them is insignificant compared to that along the narrow lubrication layer region. The membrane is assumed to possess both a shear modulus of elasticity and a non-zero bending rigidity along with the properties of preserving its surface area and enclosed volume. Neither the viscosity of the membrane nor that of the internal fluid is relevant in an axisymmetric flow problem since there is neither a tank-treading motion of the membrane nor an internal circulation, which, importantly, do not alter the pressure drop by any appreciable amount. The absence of membrane and fluid viscosities in this model will have little impact especially because the change in G and B with aspirin treatment is salient and not in their absolute values.

In addition to these stipulations, the no-slip and the axisymmetric equilibrium conditions on the cell are also enforced. While global equilibrium (also known as the 'zero-drag' condition) is automatically satisfied by the latter conditions, it is expedient to enforce this explicitly so as to readily relate the cell velocity with the average fluid velocity.

The solution strategy requires first determining the external flow field along with the shape of cell. The second step specifies the hydrodynamic loading generated by the computed flow field and enforcing the axisymmetric shell equilibrium conditions along with the material constitutive relations. These equations yield the three unknowns, B, G, and $P_i$, the constant internal pressure.

Several different approaches have been presented in the prior art to carry out the above calculations. Using perturbation methods, an analytic solution for the flow fields and shape of a cylindrical elastic membrane in simple shear flow was obtained (Rao et al., 1993). Pozrikidis (1990) obtained solutions in extensional flows using the boundary integral method. Skalak and Tozeren (1980) and Zarda et al. (1977) have used the finite element method to solve the problem of capillary flow of elastic membranes. Hochmuth and Sutera (1970) and Secomb et al. (1986) have applied the lubrication theory to produce analytic solutions in limiting situations. Finally, Leichtberg et al. (1973) have applied the multipole boundary collocation to solve the problem of rigid particles in capillary flow. The present invention uses a combination of the multipole boundary collocation method and the lubrication theory. Presented below is a step by step description of the proposed analysis.

EXAMPLE 8

In step 1, assume an axisymmetric flow and the value of the lubrication layer thickness δ. In addition, assume the cell to have a geometry of a cylinder of length l and radius a=ρ−δ, where ρ is the capillary radius, and a hemispherical end cap of radius, a at the downstream end, and another radius of b at the upstream end. Determine the values of b and l by specifying the surface area and volume of the deformed cell. Note that since specifying the volume is tantamount to enforcing the incompressibility condition, the internal pressure of the cell will now have to be determined by the cell geometrical parameters. In step 2, write a Stokes stream function formulation for the Stokes flow around the cell. In step 3, apply the boundary conditions; no slip on cell and capillary wall, Poiseuille flow far from the cell, and the zero-drag condition. In step 4, the velocity field surrounding the cell and, hence, the leak-back (the flow past the cell), given the cell velocity and δ for the above problem using the multipole boundary collocation technique is calculated. In step 5, given the pressure drop across the cell, the leak-back, and the cell velocity, δ from the Reynolds equation is calculated. In step 6, if the calculated and the assumed values of δ agree closely, one proceeds to Step 7, otherwise repeat Steps 1 through 5. In step 7, once the external flow field and the cell geometry (δ(or a), b, and l) are solved, the hydrodynamic loading on the cell is calculated and one proceeds to the shell problem. Note that the external pressure field is obtained from the Reynolds equation: $p_{ext}=-g(r)z$, where z is the axial coordinate in the direction of the flow. In step 8, one writes the axisymmetric shell equilibrium equations along with the following constitutive relations in terms of the material properties G and B:

$$t_\phi = t_m - \tfrac{1}{2} G(\lambda^2 - \lambda^{-2}), \quad (1)$$

$$t_s = t_m + \tfrac{1}{2} G(\lambda^2 - \lambda^{-2}), \quad (2)$$

$$m_s = m_\phi = B(k_s + k_\phi - (k_{s0} + k_{\phi 0})), \quad (3)$$

where $\lambda = ds/ds_0 = r_0/r$ (from membrane area conservation), $t_m$ is the mean stress resultant, and $k_s$ and $k_\phi$ are the principal curvatures of the membrane. These curvatures in the undeformed state, indicated with the subscript 0, are not conclusively defined in the literature. Some have assumed the unstressed shape of the red cell to be the biconcave disk, whereas others have assumed a spherical shape for the same. The analysis is performed under both assumptions, and the two solutions are compared with one another as well with those in the literature. It is possible that the values for B and G for the untreated cells obtained for the unstressed shape of sphere will be closer to the literature values. Regardless of which of the two is the appropriate unstressed shape, this will not significantly affect the results since the change in the material properties are more important than the values of these properties; it is likely that both before and after aspirin treatment, the data analysis is affected in a similar manner by the particular choice of the unstressed shape. In step 9, the above equations are applied for the cylindrical region at the point s=1, and write the in-plane stress resultants in terms of the internal pressure, $p_i$, the shear modulus, G, and other known quantities (a, l, and $p_{ext}$). In step 10, the same equations are applied for the downstream hemispherical end-cap, and obtain $t_m$ as a function of B,$p_{int}$ and s. Next, the normal stress equation are evaluated again at s=1. Substitute for the values of the stress resultants evaluated at this point in the previous step. Thus, obtain equation (I) relating B, G and $p_i$. In step 11, the shear stress equation on the hemispherical end-cap is written and integrated between the two end points of the generator curve, A and B. Substitute for the stress resultants the mean and deviatoric terms. The deviatoric term involves the unknown G, and the mean term is given in Step 10. This results in equation (II) relating B, G algol $p_i$. In step, the normal stress equation on the trailing hemispherical end-cap are applied. Evaluate this equation at s=0 where it is known that the in-plane stress resultants from Step 9 in terms of G and $p_i$. (Note: for a non-zero bending stiffness, the point s=0 cannot have a jump in the curvature, and so it is appropriate for the cell to have a rounded corner at this point.) Thus, we obtain equation (III) between these three variables. Consequently, equations I, II, and III can be solved for $p_i$ and the material properties, G and B. These values represent means for all the 2000 cells of a given blood sample. Such average values are obtained for red cells before and after salicylate treatment.

EXAMPLE 9

Statistical Analysis: Comparison of Transit Time Distributions

Here, the mean of the transit time distributions are compared before and after salicylate treatment using the Student's paired t-test. Also, after accounting for the difference between the means of the distribution, the two distributions are compared and checked for changes in skewness and mode. The mean cell transit times of the fastest and slowest fractions (e.g., 5%) of the population are compared. Micropipette studies demonstrate that the age of the red cell is related directly to its sphericity, and filteration experiments indicate that sphericity is similarly related to the cell transit time. Together, these correlations suggest that the cell transit time is directly proportional to the age of the cell. Consequently, if a similar change in mean cell transit time is observed among the faster and the slower cells, it indicates a lack of age dependence on the effect of salicylate.

EXAMPLE 10

Micropipette Experiments and Data Analysis

The above discussed capillary flow method is an efficient one to gather data on the red cell flow behavior, in that one can obtain the cell transit time data on about 2000 cells in as little a time as 2 minutes. In addition, the setting up of the apparatus is simple and repeatable. The same set of polycarbonate capillaries are used scores of times; they just require ultrasonication prior to each run. Thus, there is consistency in that method. The weakness in that approach, however, is that the process of deducing the membrane mechanical properties from the cell transit data is quite involved. Therefore, an alternate approach for making the membrane property determination should also be employed to cross-check results obtained by the first method.

For this purpose, one with ordinary skill in this art employs the micropipette technique which is more direct and is also the acceptable technique used by other researchers. The reason the micropipette method is not used exclusively is that it is extremely time intensive. This method will yield membrane properties, but only one cell at a time, and the time taken for each cell is not trivial. Furthermore, each micropipette must be carefully drawn so as to produce pipettes with identical geometries. Thus, this approach is even more cumbersome. Therefore, one applies the micropipette technique only to confirm the results that are obtained from the capillary flow method.

Following the methods of Waugh & Evans (1979) *Biophys. J.*, 26: 115–131 and others the membranes of individual red blood cells are aspirated into a micropipette of about 2 μm ID using suction pressures between 300 and 600 dynes/cm². The micropipette system including a test-chamber containing the red blood cells is placed on the stage of an inverted Nikon Diaphot microscope. The test-chamber consists of glass slide and cover slip separated by a thin plastic gasket on three sides. From the fourth side, a micropipette is introduced for manipulating red cells suspended in a phosphate buffered saline solution (PBS) (290 mOsmol/kg and 7.4 pH) placed between the slide and the cover slip. Individual red cells with a portion of their membrane aspirated into the micropipette is observed through a video system equipped with an image enhancer and a digitizer. The red cell membrane shear modulus of elasticity G is determined from the following relation developed by Waugh and Evans (1979) between the pipette radius, $R_p$, the length of the aspirated tongue of the membrane, L, and the applied suction pressure:

$$G=PR_p(2L/R_p-1+\ln 2L/R_p)^{-1} \quad (4)$$

The membrane viscosity, η, is determined from transient shape recovery experiments using the micropipette. Individual red cells having a point contact with the substrate (cover slip) in a PBS solution are gently pulled by a narrow micropipette (about half a micron diameter). After sufficient extension of the cell to an elongated ellipsoidal shape, the cell will recoil and recover its biconcave discoid shape in about a hundred milliseconds. The shape of the recovering red cell membrane is recorded on video 60 frames per second. A frame-by-frame measurement of the length of the cell will produce the characteristic near exponential plot of the red cell length as a function of time, t. Here, assuming a Kelvin-Voigt material the following relations apply (Smith and Hochmuth, 1982).

$$D=D_\infty \Lambda+\exp(-t/t_c)/\Lambda-\exp(-t/t_c) \quad (5)$$

where $\Lambda=D_s+D_\infty/D_m+D_\infty$ (6)

$$\eta=t_c G$$

where D is the aspect ratio (ratio of maximum dimension to the minimum dimension) of the recovering red cell, $D_m$ is the maximum or the initial aspect ratio prior to recovery, and $D_\infty$ is the final aspect ratio, which is approximately equal to 1. Thus, from a plot of the aspect ratio, D, versus time, the time constant is obtained, and having previously calculated G, η can be readily determined.

The membrane bending stiffness can be calculated from the micropipette experiments as shown by Evans (1983). In this experiment, the suction pressure, P, at which the onset of buckling occurs is recorded. The relationship between this pressure and bending rigidity, B, depends on the pipette radius, $R_p$, as well as the outer radius of the red cell $R_o$ according to the following relations:

$$B/PR^3_p=1/135, \text{ if } R_o=3, \quad (8)$$

$$B/PR^3_p=1/55, \text{ if } R_o=3, \quad (9)$$

Thus, one can determine the membrane mechanical properties of individual red cells at any given concentration of any particular salicylate.

EXAMPLE 11

Mean Cell Volume

Red cell volumes are measured using Coulter Multisizer II (Coulter, Inc., Florida) with a 1000 channelyzer interfaced with an IBM PS/2 model computer calibrated with Coulter Diagnostics blood standards. Washed, packed cells are diluted by a factor of 200,000 in PBS (isotonic media) to give cell volumes of normal discoid ($V_d$) cells. Besides mean cell volume, the Maximum mean cell volume for each sample is measured by osmotically inflating the red cells. The purpose of this procedure is to calculate the surface area of the red blood cells which remains a constant through the inflation process. Both surface area and volume are crucial to the capillary flow of a red cell. Consequently, both these quantities appear as input in the theoretical analysis. The morphological characteristics of individual cells is shown. Prior to its introduction into the capillary system, a drop of the red cell suspension in PBS on a glass slide is examined under a Nikon diaphot inverted microscope equipped with a video camera. Each suspension is observed and recorded on the video. Subsequently, the video is reviewed and the percent of echinocytes among the diskocytes is recorded.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A salicylate analogue having the structure

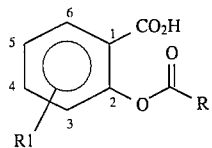

wherein R is selected from the group consisting of hexyl, octyl, nonyl, decyl, undecyl, naphthyl and cyclohexyl;

wherein R1 is selected from the group consisting of a C2–C12 alkyl group, F, Br, $CO_2H$, CONHR, $CONR_2$, $CO_2R$, C≡N, CHO, $SO_3R$, $SO_2NHR$, $SO_2NR_2$, OH, OR, SH, SR, OCONHR, $OCONR_2$, SCOR, SCONHR, $SCONR_2$, NH2, NHR, NHCOR and NR2;

and wherein R1 is in the 3-, 4-, 5- or 6-position, or a combination thereof.

2. A pharmaceutical composition, comprising the salicylate analogue of claim 1 and a pharmaceutically acceptable carrier.

3. A salicylate analogue of claim 1 having the chemical name benzoic acid, 2-(1-oxononyloxy).

4. A salicylate analogue of claim 1 having the chemical name benzoic acid, 2-(1-oxo-2-methylpropoxy).

5. A salicylate analogue of claim 1 having the chemical name benzoic acid, 2-(1-oxo-3-methylbutyl)oxy.

6. A salicylate analogue of claim 1 having the chemical name benzoic acid, 2-(1-oxoundecyl)oxy.

7. A salicylate analogue of claim 1 having the chemical name benzoic acid, 2-(cyclohexylcarbonyl)oxy.

8. A salicylate analogue of claim 1 having the chemical name benzoic acid,2-(1-naphthoyl)oxy.

9. A salicylate analogue of claim 1 having the chemical name benzoic acid, 5-fluoro-2-(1-oxobutyl)oxy.

* * * * *